United States Patent [19]

Kudla et al.

[11] Patent Number: 5,284,632

[45] Date of Patent: * Feb. 8, 1994

[54] TWO-TIERED STERILIZATION AND STORAGE CASSETTE

[75] Inventors: James M. Kudla, Mount Prospect; Roy E. Riihimaki, Libertyville, both of Ill.

[73] Assignee: Hu-Friedy Mfg. Co., Inc., Chicago, Ill.

[*] Notice: The portion of the term of this patent subsequent to Jun. 1, 2010 has been disclaimed.

[21] Appl. No.: 996,679

[22] Filed: Dec. 24, 1992

Related U.S. Application Data

[63] Continuation of Ser. No. 731,422, Jul. 17, 1991, Pat. No. 5,215,726.

[51] Int. Cl.$^5$ .............................................. A61L 2/06
[52] U.S. Cl. ............................ 422/297; 422/300; 206/263; 206/363; 206/369; 206/370; 206/438; 206/565
[58] Field of Search ............... 422/297, 300, 310, 104; 206/210, 263, 363, 369, 370, 438, 480, 483, 565, 635

[56] References Cited

U.S. PATENT DOCUMENTS

| D. 295,075 | 4/1988 | Jerge et al. | D24/9 |
|---|---|---|---|
| 1,157,733 | 10/1915 | Stevenson . | |
| 1,471,050 | 10/1923 | Montag . | |
| 2,147,510 | 2/1939 | Amick | 206/263 |
| 3,285,409 | 11/1966 | Loran | 206/564 X |
| 3,330,434 | 7/1967 | Bromley | 220/4 |
| 3,890,096 | 6/1975 | Nichol et al. | 21/105 |
| 4,046,254 | 9/1977 | Kramer | 206/370 |
| 4,135,868 | 1/1979 | Schainholz | 422/310 |
| 4,327,060 | 4/1982 | Nisii | 422/300 |
| 4,333,567 | 6/1982 | Leonard | 206/368 |
| 4,541,992 | 9/1985 | Jerge et al. | 422/300 |
| 4,577,755 | 3/1986 | Ramsay | 206/370 |
| 4,854,475 | 8/1989 | Riihimaki et al. | 220/337 |
| 4,865,821 | 9/1989 | Langdon | 422/300 |
| 4,959,199 | 9/1990 | Brewer | 422/300 |
| 4,978,510 | 12/1990 | Smith | 422/310 |
| 5,084,251 | 1/1992 | Thomas | 422/300 |
| 5,098,676 | 3/1992 | Brooks, Jr. | 422/292 |
| 5,127,537 | 7/1992 | Graham | 220/339 |

OTHER PUBLICATIONS

Svenska Dental Instruments AB, Vasby, Sweden, Applicants' Reference ("AR").
Syntex Dental Products, Bay Minette, Ala. Mar. 1982, Applicants' Reference ("AS").
A-dec Trays & Tubs, Newberg, Ore., Applicants' Reference ("AT").
Medin Corporation, Instrument Tray For Microsurgery, Applicants' Reference ("AAR").
Aesculap, Tuttlingen, West Germany, Applicants' Reference ("AAS").
Winston-Salem Dental Care Plan, Inc., Winston-Salem, North Carolina, Applicants' Reference ("AAT").

Primary Examiner—James C. Housel
Assistant Examiner—Milton I. Cano
Attorney, Agent, or Firm—Dressler, Goldsmith, Shore & Milnamow, Ltd.

[57] ABSTRACT

A sterilizable instrument cassette for use in storage and sterilization of medical and dental instruments includes two individual storage trays with base plates carrying silicone instrument-locating rails, and rotatable clamping members provided with silicone compression rails. The two trays may be separated or assembled and latched together, while the rotatable clamping member may be latched in its closed position. Multiple functions are performed by unitary structures simply and economically formed from single sheets of metal by stamping and bending.

20 Claims, 4 Drawing Sheets

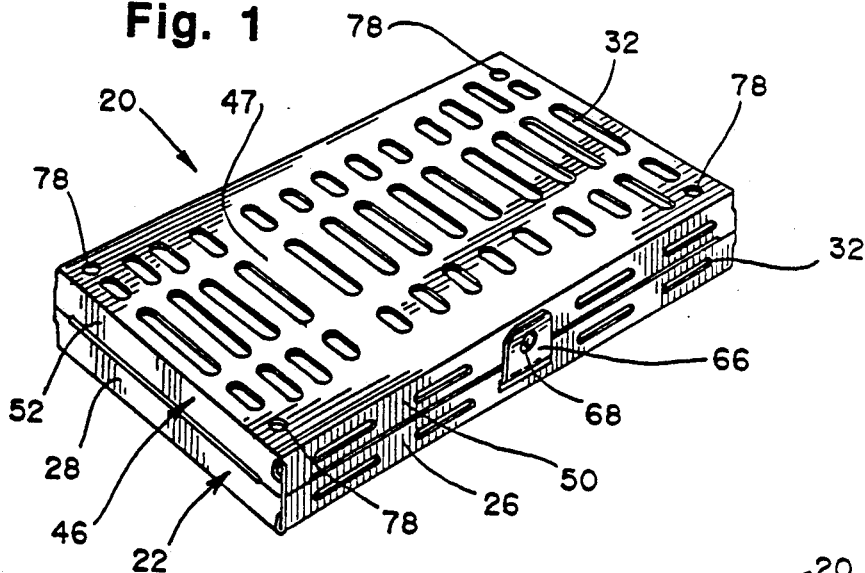
Fig. 1
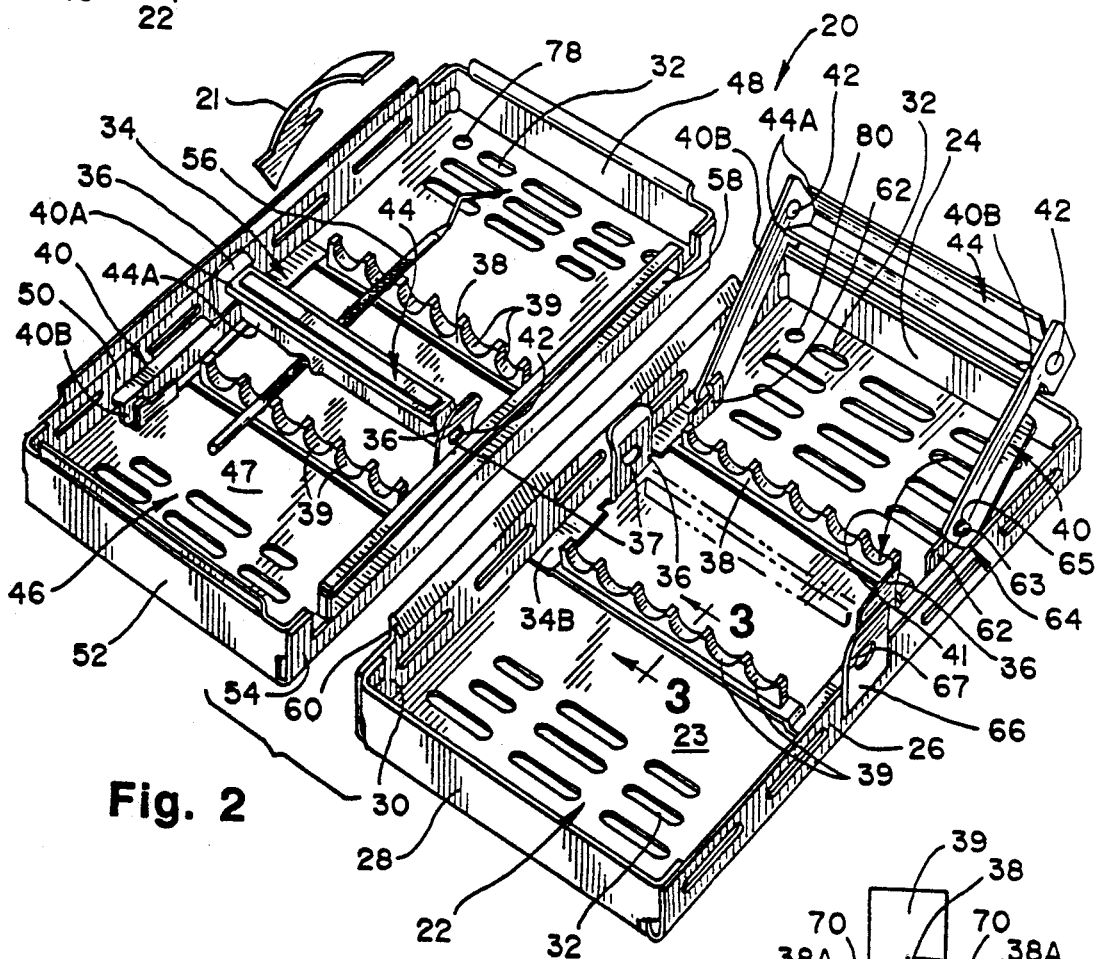
Fig. 2
Fig. 3

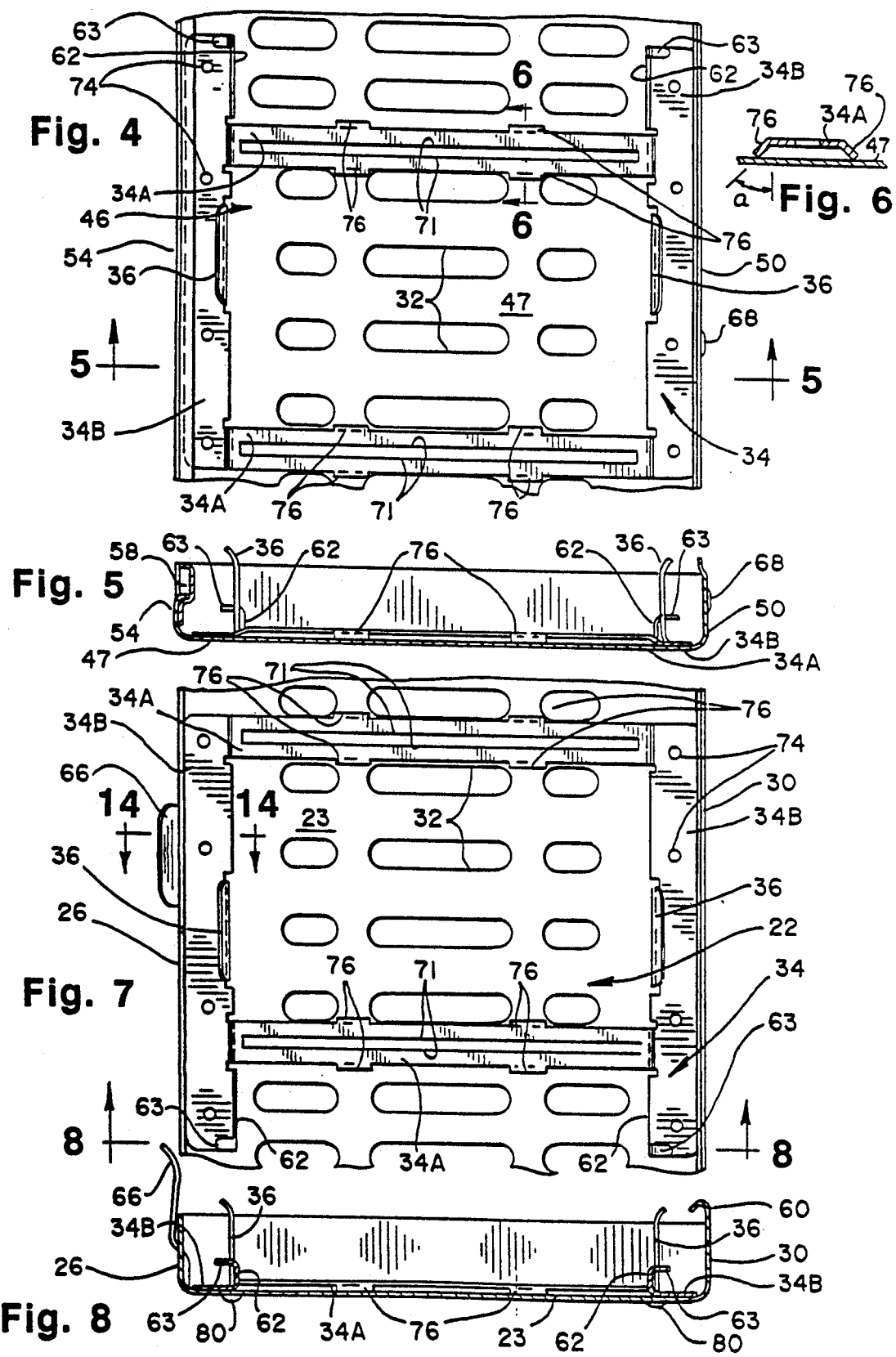

TWO-TIERED STERILIZATION AND STORAGE CASSETTE

This application is a continuation of application Ser. No. 07/731,422, filed Jul. 17, 1991, now U.S. Pat. No. 5,215,726.

FIELD OF THE INVENTION

This invention relates to a medical/dental instrument sterilization cassette. More particularly, it relates to a two-tiered cassette capable of holding two levels of instruments.

BACKGROUND OF THE INVENTION

Medical and dental instruments used in both routine examinations and more complicated surgeries require sterilization before use. In the past, these instruments have been sterilized either as individual instruments loosely placed in the autoclave or organized in plastic or metal storage cassettes. However, both these methods have led to certain problems.

When loose instruments are individually placed in the autoclave and not secured, they may strike against each other or against the interior of the autoclave, causing harmful metal-to-metal contact. Since the instruments are delicate in nature, the resulting contact can cause damage and render them useless or subject to contamination. Additionally, because the instruments are not secured in any set order, they must be reorganized before the next surgical procedure. This process is time-consuming, and when instruments from different types of surgeries are autoclaved together, even more time is spent on sorting and reorganizing the specific instruments for each type of surgery.

On the other hand, when instruments are sterilized and organized in conventional cassettes, a different set of problems arises. At lower production volumes, metal cassettes are cheaper than plastic cassettes but when these metal cassettes are normally constructed from reinforced wire mesh they are subject to rust, discoloration, breakage, and debris entrapment. Secondly, wire cassettes are not stackable, and therefore take up too much space during autoclaving and storage. Thirdly, when the instruments are placed into these cassettes, metal-to-metal contact again occurs between the instruments and the cassette. This contact causes the same problems as when the instruments are sterilized loosely, inasmuch as the instruments become damaged or scratched and thus subject to contamination.

Still another problem arises with conventional metal trays used for sterilization and storage of medical and dental instruments. Currently, the instruments are held in place only by closing the cassette cover. If the cover loosens or is not properly secured, it may release during the loading and unloading of the trays from the autoclave or from storage. Because the instruments are not otherwise secured within the cassette, they may fall out and be damaged. Furthermore, if instruments are loose within a cassette, the same damaging metal-to-metal contact between instruments, or between instruments and the cassette, may occur.

Finally, there is a problem with the amount of storage available for medical and dental instruments in the cassettes now available. In U.S. Pat. No. 4,854,475, for example, space for placing and securing instruments is only provided in the bottom portion of the cassette, while the covers are left unutilized. As a result, fewer instruments may be sterilized at one time, which leads to more time spent autoclaving. This lack of space management not only affects autoclaving time, but also limits storage space for the instruments after they emerge from the autoclave.

U.S. Pat. No. 4,959,199 partly addresses this problem, in that it provides an instrument sterilization cassette which separates into individual trays, each capable of storing instruments and each having a cover member which helps to retain the instruments in place therein. But the cover member is completely detachable from the tray, and when separated may become lost. In addition, the cassette of this patent is entirely molded from plastic resin materials, a method of manufacture which is relatively expensive at low production volumes.

Because of these considerations, there exists a need to provide a two-tier cassette to hold medical and dental instruments during and after sterilization, which overcomes the above-mentioned disadvantages, and which can, if desired, be manufactured largely from sheet metal stampings.

SUMMARY OF THE INVENTION

It is therefore an object of the present invention to provide a stackable instrument cassette which may be used by medical or dental personnel for the storage and sterilization of medical and dental instruments.

It is another object of the present invention to provide a two-tier instrument cassette which can be fabricated of sheet metal and which utilizes both its bottom and top sections to hold medical and dental instruments.

In accordance with these objectives, the present invention provides an instrument sterilization and storage tray comprising means to define a plurality of fixed instrument positions in the tray, clamping means, and mounting means attaching the clamping means to the tray and mounting the clamping means for rotation, while so attached, into and out of a position for clamping the instruments in place in their fixed positions. In a preferred embodiment of the invention, there are two such trays which cooperate to form a cassette.

In accordance with additional features of the invention which make it easier to fabricate, the rotatable mounting means comprises base plate means fixed to the tray, respective hinge means on the base plate means and on the clamping means cooperating with each other, with one of the hinge means comprising a projection and the other comprising a receptacle for the projection.

In addition, it is contemplated that there will be respective means on the base plate means and on the clamping means for releasably locking the clamping means in an instrument-clamping position when rotated into the clamping position about the hinge means. One of the releasable locking means may comprise flexible latching plate means including a detent, and the other may comprise projection means for flexing the latching plate and engaging the detent.

It is further contemplated that the clamping means will comprise compression rail means for yieldably clamping the instruments. The compression rail may also be releasably fastened to the clamping means so that it can easily be mounted thereon during fabrication and easily removed therefrom for cleaning and/or replacement.

A cooperating instrument-locating rail below each clamp means is similarly constructed so that it is releasably fastened to the base plate and is also easily mounted thereon during fabrication and easily removed therefrom for cleaning and/or replacement.

When using the two-tiered cassette, one first unlatches and opens it, thereby exposing top and bottom trays for placing and securing medical and dental instruments. To load the instruments, the clamping means on each tray is unlatched and rotated, allowing the instruments to be placed in the trays, along the instrument-locating rails and organized in the order required for a particular dental or surgical procedure. After the instruments are loaded, the clamping means is then rotated into and secured in a closed position by latch means. The compression rail attached to the clamping means deforms to accommodate the shapes of the instruments, thus creating a confined and secure fit for different sizes and shapes of instruments.

When both trays are filled with instruments, they are hinged together, rotated into a superposed relationship, and secured together by means of a latch-type fixture. The fully loaded two-tiered cassette is then ready for stacking during sterilization in the autoclave, and subsequently for efficient storage of the instruments.

The above, as well as other objects and advantages of the invention, will become apparent from the following detailed description of an illustrative embodiment of the invention, in which reference is made to the accompanying drawings.

BRIEF DESCRIPTION OF THE DRAWINGS

FIG. 1 is a perspective view of a preferred embodiment of a two-tier instrument cassette in accordance with the invention, depicted in a closed position, in which the top and bottom tiers each form a separate instrument storage and sterilization tray.

FIG. 2 is a perspective view of the same cassette, but with the top and bottom trays of the cassette opened and unhinged, with one clamping mechanism opened and the other closed to secure a typical dental instrument.

FIG. 3 is a fragmentary cross-section taken along line 3—3 of FIG. 2, depicting a portion of the internal base plate and instrument-locating rails, showing the releasable tongue-in-groove connection between the base plate and the instrument-locating rails.

FIG. 4 is a fragmentary plan view of the top tray in its open position.

FIG. 5 is a cross-section taken along line 5—5 of FIG. 4.

FIG. 6 is a fragmentary cross-section taken along line 6—6 of FIG. 4, depicting the elevated cross-member of the base plate.

FIG. 7 is a fragmentary top plan view of the bottom tray in its open position.

FIG. 8 is a cross-section taken along line 8—8 of FIG. 7.

In the various figures of the drawing, like parts are indicated by like reference characters.

DETAILED DESCRIPTION OF THE PREFERRED EMBODIMENT

Figure 9:
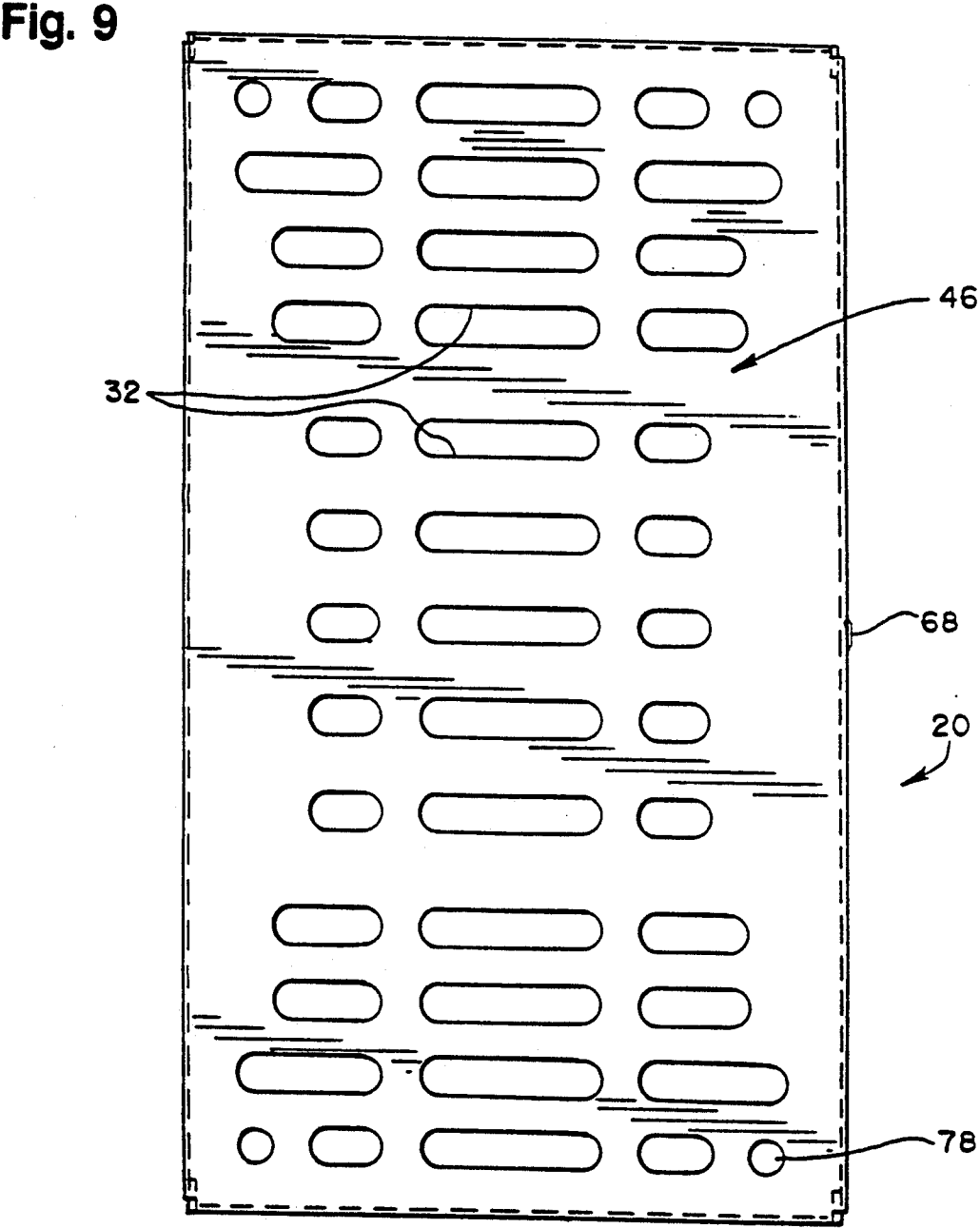
FIG. 9 is a top or bottom plan view of the cassette, depicting the layout of the fluid passage openings in both the top wall of the top tray and the bottom wall of the bottom tray.

In accordance with this invention, a two-tiered medical/dental instrument cassette, generally designated 20, is provided to aid in the storage and sterilization of medical and dental instruments. The cassette 20 comprises two separate trays, a lower one 22 and an upper one 46. Lower tray 22, of generally rectangular configuration, has a floor member 23, four upstanding sidewalls 24, 26, 28, 30, a base plate 34, two instrument-locating rails 38, a rotatable clamping member 40, and a compression rail 44. The top tray 46, also of generally rectangular configuration, similarly has a ceiling member 47, four depending sidewalls 48, 50, 52, 54, a base plate 34, two instrument-locating rails 38, a rotatable clamp member 40, and a compression rail 44. The floor, ceiling and sidewall members are perforated by fluid-passage openings 32 to facilitate the ingress and egress of sterilizing fluids such as steam.

The floor and ceiling members, as well as all tray sidewalls, base plates and rotatable clamp members, are constructed out of stainless steel or other heat-resistant metallic material which may be sterilized in an autoclave before re-use. At lower production volumes, it has been found that it is substantially easier and less expensive to fabricate the disclosed structure out of sheet metal stampings than to create the dies necessary to mold it out of plastic resin.

The top tray 46 and bottom tray 22 are separably connected by means of a hinge formed by a top tray hinge member 58, running along the edge of the top tray sidewall 54, which cooperates with a bottom tray hinge member 60, running along the edge of the bottom tray sidewall 30. The interaction between members 58 and 60 permits the top tray 46 and the bottom tray 22 to swing between open and closed positions relative to each other. The top and bottom tray are also separable from one another after opening the hinge 58, 60 of the cassette 20, thereby allowing individual access to each tray. The hinge 58, 60 is of the type more fully disclosed and explained in U.S. Pat. No. 4,854,475.

As seen in FIGS. 2, 4 and 5, the top tray hinge member 58 is in the form of a channel or receptacle running lengthwise near the edge of the top tray sidewall 54, which is recessed into the interior of the top tray 46. As seen in FIGS. 2 and 8, the bottom tray hinge member 60 is an angled flange running lengthwise along the edge of the bottom tray sidewall 30, which bends inwardly towards the interior of the bottom tray 22. When joining the two trays, the top tray 46 is placed at approximately a ninety degree angle to the bottom tray 22, such that the channel of the top tray hinge member 58 receives the flange of the bottom tray hinge member 60. The top tray is then rotated down over the bottom tray in the direction opposite to arrow 21 in order to close the cassette 20.

Figure 10:
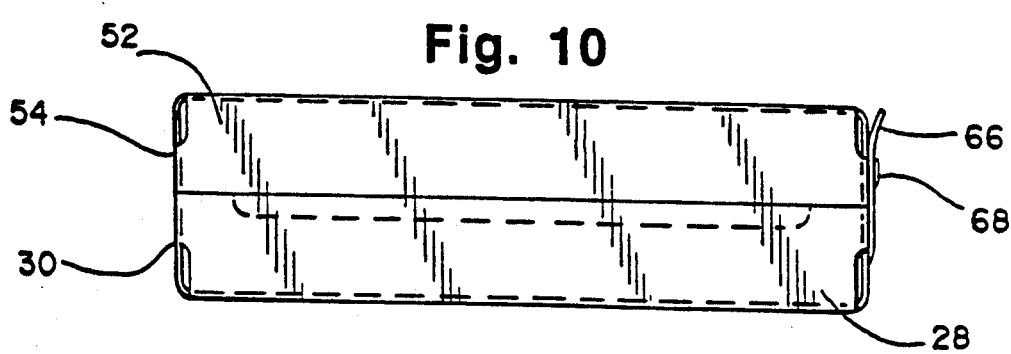
FIG. 10 is an end elevation of the cassette.

When the two trays are closed, as seen in FIG. 10, the bottom and top sidewalls 30 and 54 are co-planar, providing a flat back surface for the stable upright placement of the closed cassette 20. Two additional co-planar surfaces for stable upright placement of the cassette are also created by the bottom and top sidewalls 24, 48 and the bottom and top sidewalls 28, 52 when the cassette 20 is closed.

Figure 14:
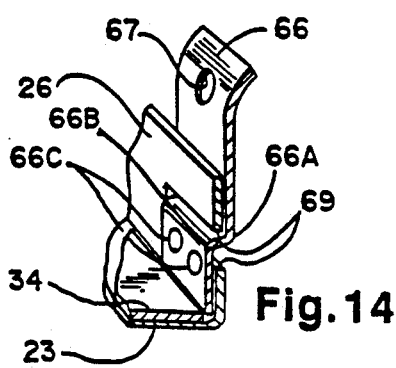
FIG. 14 is a fragmentary cross-section taken along line 14—14 of FIG. 7, depicting a latch-type fixture which facilitates closure of the top and bottom trays.
Figure 13:
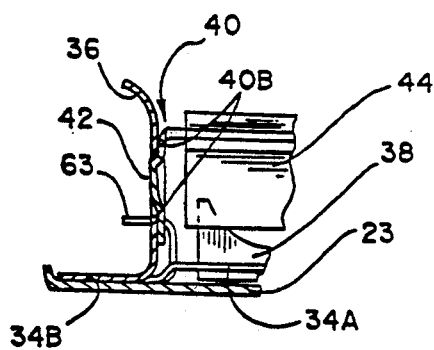
FIG. 13 is a similar cross-section taken along line 12—12 of FIG. 11, depicting the latch-type fixture with the clamp mechanism closed and latched in place.

Latch means are provided to secure the bottom tray 22 to the top tray 46 once the cassette 20 is in the closed position. A flexible bottom tray latch plate 66 with a hole 67 punched out of it extends above the bottom tray sidewall 26, and is centrally located along said sidewall in order to cooperate with a top tray latch button 68. As seen in FIG. 14, latch plate 66 extends through slot 69 in sidewall 26 and bent with two approximately 90 degree bends 66A and 66B to achieve its upright position. Said latch plate 66 is fixedly connected to sidewall 26 by means of spot welds 66C on the inside of sidewall 26. The latch button 68 projects outwardly from the center of the top sidewall 50. When the top tray 46 closes over onto the bottom tray 22, the latch button 68 flexes the plate 66 outwardly until it reaches and enters the hole 67. Thus, as seen in FIGS. 1 and 10, latch members 66 and 68 join together to secure the cassette in the closed condition.

The hinge and latch members described above are also constructed out of a stainless steel or other heat-resistant metallic material which may be sterilized in an autoclave before re-use.

The interior structures of the upper and lower trays are identical. Within each tray 22 and 46 there is a base plate 34 and a rotatable clamping member 40. Each base plate comprises a bridge portion 34A which extends across the floor member 23 or ceiling member 47, and pedestal strips 34B, which run along the edges of the floor member or ceiling member. The pedestal strips 34B are fixedly connected to the tray floor by means of spot welds 74 (FIGS. 4 and 8) Each bridge portion 34A is raised above the floor member or ceiling member by means of the pedestal strips 34B and also by means of flanges 76 which extend downward from bridge portions 34A preferably at an angle a of about 35 degrees from the vertical (FIGS. 5, 6 and 8).

Figure 11:
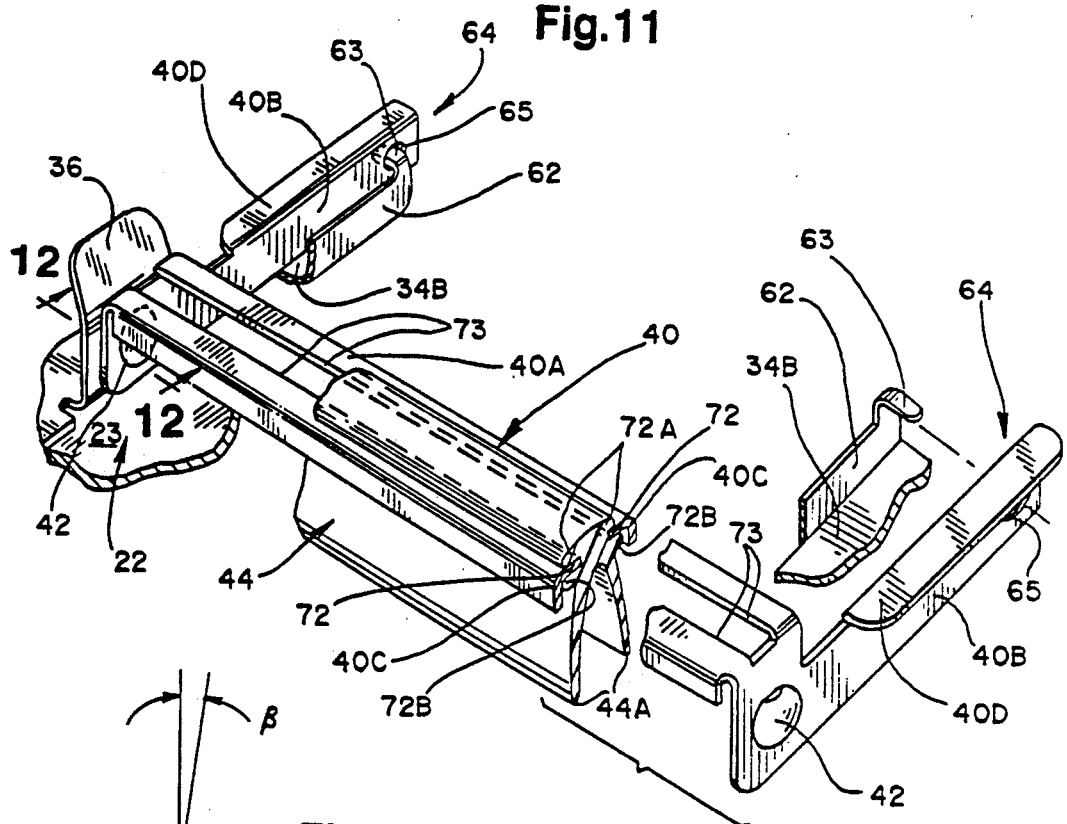
FIG. 11 is a perspective view of the clamping mechanism of the cassette, with parts broken away for clarity of illustration, and also illustrating other portions of the cassette which cooperate therewith.
Figure 12:
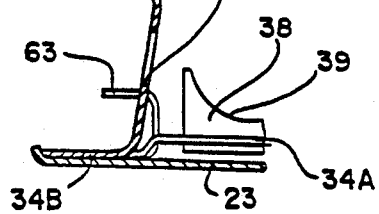
FIG. 12 is a fragmentary cross-section taken along line 12—12 of FIG. 11, depicting a latch-type fixture which cooperates with the clamping mechanism, with the clamp rotated out of view.

Each rotatable clamping member 40 is releasably attached to its base plate 34 by means of a hinge assembly 64. As shown in FIGS. 2 and 11, this hinge assembly 64 includes flanges 62 extending upwardly from a portion of each base plate pedestal strip 34B, and are further formed with tabs 63 extending horizontally towards sidewalls 26, 30 which serve as hinge pins. The clamping members 40 each include cross-members 40A and a pair of side-members 40B, and each of the latter is formed with a hole 65 to accept one of the hinge pin tabs 63. Thus, each clamping member 40 is rotatable about a pair of hinge tabs 63. This hinged connection allows each clamping member 40 to rotate (see arrow 41 in FIG. 2) from the open position illustrated at the right of FIG. 2 to the closed position illustrated at the left of FIG. 2, in which it clamps an instrument 56 in place.

The clamping member 40 is further provided with cross-member stiffeners 40C and side-member stiffeners 40D to stiffen and strengthen clamping member 40. As seen in FIG. 11, cross-member stiffeners 40C are angled flanges running along both sides of cross-member 40A, which bend downwardly from the top of cross-member 40A at approximately a 90 degree angle. Similarly, side-member stiffeners 40D are angled flanges running along the top of side-members 40B. Side-member stiffeners 40D are bent outwardly from the tops of the side-members 40B at approximately a 90 degree angle. Side-member stiffeners 40D in conjunction with each side-member 40B thus create an L-shaped beam, while cross-member stiffeners 40C in conjunction with each cross-member 40A thus create a U-shaped beam. The entire rotatable clamping member 40 with its cross-members 40A, side-members 40B and related stiffeners 40C, 40D are all manufactured from a single sheet metal stamping which is then bent to form the finished clamping member 40.

The clamping members 40 may easily be released from or assembled with the base plate 34 by flexing the side-members 40B toward each other to facilitate withdrawal of the hinge tabs 63 from, or insertion into, the holes 65. This feature makes it easy to manufacture the cassette of this invention during initial production, and also facilitates subsequent disassembly for repair or cleaning purposes, and reassembly thereafter.

Each base plate 34 and rotatable clamping member 40 is provided with latch-type means to secure the clamping member in the closed position. As shown in FIGS. 2, 11, 12, and 13, a flexible latch tongue 36 is integral with and bent upwardly from each pedestal strip 34b at each side of each base plate 34. These latch plates 36 slant inwardly at an angle $\beta$ of about three degrees towards the center of the tray 22 or 46 (see FIG. 12), and have a latch-receiving hole 37 punched therein. Each rotatable clamping member 40 is formed with convex latch buttons 42 punched outwardly from each side-member 40B thereof. (See FIGS. 2, 11 and 13).

When one of the clamping members is rotated into the clamping position, latch buttons 42 flex the tongues 36 outwardly until the buttons enter the holes 37, thus securing the rotatable clamping member 40 in its clamping position. In order to release any of the clamping members, it is only necessary to manually flex apart the two tongues 36 which latch that clamping member, and lift the clamping member until its buttons 42 pull free of their cooperating holes 37.

The base plates 34 and rotatable clamping members 40, along with all their component parts, are constructed out of stainless steel or other heat-resistant metallic material which may be sterilized in an autoclave before re-use. The inherent springiness of such materials permits the necessary flexure of the latch tongues 36 and side-members 40B.

Instrument-locating rails 38 are provided to define storage positions for the sterilizable medical or dental instruments, such as instrument 56 in FIG. 2, and to separate them from adjacent instruments (not shown). The instrument-locating rails 38 are scalloped to define recesses 39 spaced across the width of each tray 22 and 46, and serve to locate instruments, such as the instrument 56, in an ordered fashion. Additionally, because the individual scallops 39 are separated from each other, they serve to separate adjacent instruments. The scallops 39 further serve to hold the instruments away from the cassette tray surface 23 or 47 because the instrument-locating rails 38 are raised above surfaces 23 and 47 by the flanges 76. Thus, the instruments are effectively isolated from one another and from all parts of the cassette, and therefore cannot be damaged by contact with either the cassette or other instruments.

Instrument-retaining rails 44 are mounted on the cross-members 40A of clamping members 40 to make contact with the instruments and thus lock them in place within the recesses 39 when the clamps are rotated into the clamping position. These rails 38, 44 are both formed of a resiliently compressible but autoclavable material, such as silicone rubber, so that when instruments 56 are stored in the cassette 20 or sterilized therewith, the instruments are not damaged.

These resilient rails 38 and 44 are removably fastened to the base plates 34 and the cross-members 40A of the rotatable clamping members 40 respectively. As seen in FIG. 3, instrument-locating rails 38 are formed with pairs of upper flanges 38A and lower flanges 38B which define between them receptacle grooves 70 running lengthwise along each side of the rails 38. As seen in FIGS. 4 and 7, from which the resilient rails 38 have been removed for clarity of illustration, each base plate cross-member 34A is formed with a longitudinal slot having pairs of internal edges 71, which are received within the receptacle grooves 70, thus connecting the instrument-locating rails 38 to their base plates 34.

The instrument-retaining compression rails 44, as seen in FIG. 11, similarly have receptacle grooves 72 formed by upper flanges 72A and lower flanges 72B. The cross-members 40A of clamping members 40 are also formed with longitudinal slots having pairs of internal edges 73, which are received within the receptacle grooves 72 to mount the compression rails 44 upon the cross-members 40A. When any of the rotatable clamping members 40 are rotated to the closed position seen at the left in FIG. 2, a pair of compressible skirts 44A depending from each of the compression rails 44 (see also FIG. 11) presses resiliently against the instrument 56 to keep it locked with its own scallop or recess 39, so that it cannot escape to experience metal-to-metal contact with any other instrument 56 or any part of the cassette structure.

The inherent flexibility of the silicone rubber material of which the rails 38 and 44 are formed permits them to be easily distorted as necessary for inserting them into their respective slots formed in the cross-members 34A and 40A, and for inserting the respective slot edges 71 and 73 thereof into the grooves 70 and 72 respectively. This facilitates initial production of the cassette 20, as well as subsequent disassembly and reassembly of the cassette 20 for cleaning and/or repair.

At this point in the discussion it will readily appreciated that each base plate 34 provides, in a single structure, a cross-member 34A for supporting the instrument-locating rail 38, multiple flanges 76 for supporting the cross-members 34A off the floor 23 or ceiling 47, a pair of hinge tabs 63 for the clamping members 40, a pair of latching tongues 36 for the clamping members, and a pair of pedestal members 34B which are used to attach the entire base plate 34 to the floor 23 or ceiling 47. This fact substantially simplifies the assembly of the cassette 20. In addition, the entire base plate 34 can readily be fabricated out of a single piece of sheet metal by stamping and bending, which simplifies the manufacture of the base plate and reduces the attendant expense for labor and materials involved in production.

Similarly, each clamping member 40 includes a pair of hinge receptor holes 65, the cross-member 40A, with cross-member stiffeners 40C, which mounts its associated compression rail 44, side members 40B with side-member stiffeners 40D, and a pair of latch buttons 42. This member is also formed from a single piece of sheet metal by stamping and bending, which has the same manufacturing advantages.

As shown in FIGS. 1 and 2, stacking receptor depressions 78 are provided on the top surface of top tray 46 to accept stacking feet 80 (see FIG. 8) correspondingly located on the bottom surface of bottom tray 22. The receptor depressions 78 are preferably formed by punching holes through ceiling member 47, whereas the feet 80 are formed by spherical or similarly shaped protrusions punched downwardly from floor member 23. The locations of the receptor depressions 78 and feet 80 are coordinated so that the bottom tray 22 of an upper cassette 20 and the top tray 46 of a lower cassette 20 align with each other when the cassettes are stacked atop one another, thus allowing an assembled cassette, or a plurality of such cassettes, to be stacked during storage and/or sterilization. Additionally, this configuration of feet and receptors creates a locking action which prevents lateral sliding of one cassette relative to another.

The operation of the invention will now be described. The closed cassette, illustrated in FIG. 1, is opened, as suggested by arrow 21 in FIG. 2, exposing both the top and bottom base plates 34, instrument-locating rails 38, rotatable clamping members 40, and compression rails 44.

To locate the medical or dental instruments 56 within the cassette, the user first opens the rotatable clamping members 40 by flexing their latch tongues 36 away from each other to release the rotatable clamping member latch buttons 42 (see FIGS. 12 and 13). once released, each clamp 40 is rotated to the open position about its hinge pins 63 in the direction opposite to arrow 41 in FIG. 2, thereby exposing the instrument-locating rails 38 and their scalloped recesses 39. The user then places each instrument 56 within aligned recessed 39 of two parallel instrument-locating rails 38 of either tray 22 or 46, thus orienting the instrument 56 longitudinally to the cassette 20. The recesses 39 allow the instruments 56 to be individually placed in an organized and ordered fashion, according to either the type of instruments being loaded or the type of surgical procedure in which the instruments will be used. Instruments are placed within the cassette until all the recesses 39 of both the top and bottom trays 22, 46 are full, or there are no more instruments to be sterilized and/or stored.

Once the instruments are located in their proper place and order, the user then secures them in the tray. As seen in FIG. 2, each rotatable clamping member 40 is pivoted about its hinge as shown by arrow 41 until it closes on top of the instruments and snaps into place by means of the latch members 37 and 42. Because the latch tongues 36 are angled inward, the rotatable clamping member latch buttons 42 enter the latch openings 37, allowing the latch tongues 36 to spring inwardly toward each other and thereby lock the buttons 42 in place when they align with the openings 37.

When both the top and bottom trays 46 and 22 are filled with instruments and the clamping members 40 secured, the user then reassembles the cassette 20 by placing the bottom tray hinge member 60 into the top tray hinge member 58 and rotating the top tray 46 in the direction contrary to arrow 21 of FIG. 2. After the cassette 20 is closed and latched by means of the latch members 66 and 68, it is then ready for autoclaving or storage. For ease and efficiency, the stacking receptors 78 and stacking feet 80, and/or the co-planer surfaces created by the joining of the sidewalls, 24, 48 and 28, 52, allow the cassette to be stacked either vertically or horizontally during storage or during sterilization within the autoclave.

In keeping with the manufacturing philosophy set forth above, the tray members 23, 26, 28, 30, 32 are all formed from a single sheet of metal by stamping and bending, and tray members 47, 48, 50, 52, 54 similarly are all formed from a single sheet of metal by stamping and bending. Therefore a simple and inexpensive method of creating the stacking feet 80 is for them to take the form of convex dimples punched outwardly of the ceiling member 47, and a corresponding method of creating the stacking receptors 78 is for them to take the form of concave dimples punched inwardly of the floor member 23 or preferably holes punched entirely through the floor member.

While the principles of the invention have been described above in connection with a specific embodiment, this description is intended only by way of example and not as a limitation on the scope of the invention, which is stated more broadly in the appended claims.

The invention claimed is:

1. A sterilization and storage cassette comprising:
first and second trays connectable with each other, wherein each of said trays has at least one instrument locating rail, wherein each of said at least one rail has first and second ends, and first and second rotatable clamping members wherein each of said members is affixed to a said respective tray at first and second pivot points adjacent to said ends and wherein each of said rotatable clamping members is independently rotatable relative to its respective tray about an axis that extends parallel to said at least one rail from a secured position to an open position.

2. A sterilization and storage cassette in accordance with claim 1 which includes a hinge connection between said trays.

3. A sterilization and storage cassette in accordance with claim 1 wherein each of said trays includes a plurality of said instrument locating rails.

4. A sterilization and storage cassette in accordance with claim 1 wherein said instrument locating rails are detachable from their respective trays.

5. A sterilization and storage cassette in accordance with claim 1 wherein each of said rotatable clamping members includes a compression rail.

6. A sterilization and storage cassette in accordance with claim 1 wherein said rotatable clamping members are detachable from their respective trays.

7. A sterilization and storage cassette in accordance with claim 1 wherein each of said trays has a plurality of fluid passage openings.

8. A sterilization and storage cassette in accordance with claim 1 wherein each of said trays has a plurality of stacking feet and stacking receptors.

9. A sterilizable instrument cassette comprising:
a pair of cassette components including at least one tray;
a hinge to join said tray and said other cassette component together to form said cassette;
a rail defining a plurality of instrument storage positions in said tray said rail having first and second ends;
a clamping member; and
mounting means for rotatably attaching said clamping member to said tray at first and second spaced apart locations adjacent to said ends, wherein said clamping member is rotatable about an axis that extends parallel to said rail into and out of a position for clamping instruments in place in said storage positions.

10. A sterilizable instrument cassette in accordance with claim 9 wherein said other cassette component is a second tray, and further comprising:
a second rail in said second tray defining a plurality of instrument storage positions therein;
a second clamping member; and
mounting means for rotatably attaching said second clamping member to said second tray, wherein said second clamping member is rotatable about an axis that extends parallel to said second rail into and out of a position for clamping instruments in place in said storage positions.

11. A sterilizable instrument cassette comprising:
a pair of cassette components including first and second trays;
a hinge to join said trays together to form said cassette;
elongate means for defining a plurality of spaced apart instrument positions in each of said trays;
clamping means in each of said trays; and
first and second mounting means rotatably attaching said clamping means to each of said trays, wherein said mounting means each includes first and second spaced apart elongated support members coupled to said clamping means and wherein each of said clamping means is rotatable about an axis that extends parallel to said elongated means into and out of an instrument clamping position.

12. A sterilizable instrument cassette in accordance with claim 11 wherein said means to define a plurality of spaced apart instrument positions includes an instrument locating rail.

13. A sterilization and storage cassette comprising:
a tray and a cover connectable to each other, wherein said tray has an elongated instrument locating rail with first and second ends and a rotatable clamping member affixed to said tray at two spaced apart pivot points adjacent to said ends, and wherein said rotatable clamping member is independently rotatable relative to said tray about an longitudinal axis that extends parallel to said rail from a secured position to an open position.

14. A cassette in accordance with claim 13 which includes a hinge connection between said tray and said cover.

15. A cassette as in claim 13 wherein said cover includes a second tray.

16. A cassette in accordance with claim 15 wherein each of said trays includes a plurality of said instrument locating rails.

17. A cassette in accordance with claim 16 wherein said instrument locating rails are detachable from their respective trays.

18. A cassette in accordance with claim 13 wherein each of said rotatable clamping members includes a compressible rail.

19. A cassette in accordance with claim 13 wherein said rotatable clamping member is detachable from said tray.

20. A cassette as in claim 13 wherein said clamping member is U-shaped.

* * * * *